United States Patent [19]

Lee et al.

[11] Patent Number: 5,747,065
[45] Date of Patent: May 5, 1998

[54] MONOGLYCERIDE/LACTATE ESTER PERMEATION ENHANCER FOR OXYBUTYNIN

[76] Inventors: Eun Soo Lee, 108 W. Danbury, Redwood City, Calif. 94061; Tyler Watanabe, 709 Panchita Way; Robert M. Gale, 1276 Russel Ave., both of Los Altos, Calif. 94022; Terry L. Burkoth, 711 Torreya, Palo Alto, Calif. 94303

[21] Appl. No.: 617,763

[22] PCT Filed: Sep. 29, 1994

[86] PCT No.: PCT/US94/11226

§ 371 Date: Mar. 15, 1996

§ 102(e) Date: Mar. 15, 1996

[87] PCT Pub. No.: WO95/09007

PCT Pub. Date: Apr. 6, 1995

Related U.S. Application Data

[63] Continuation-in-part of Ser. No. 129,494, Sep. 29, 1993, abandoned.

[51] Int. Cl.$^6$ .................................................. A61F 13/02
[52] U.S. Cl. .......................... 424/448; 424/449; 514/946; 514/947
[58] Field of Search ................................ 424/448, 449; 514/946, 947

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,551,554 | 12/1970 | Herschler | 424/7 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 3,987,052 | 10/1976 | Hester | 260/308 |
| 4,006,218 | 2/1977 | Sipos | 424/54 |
| 4,031,894 | 6/1977 | Urquhart et al. | 128/268 |
| 4,046,886 | 9/1977 | Smith | 424/227 |
| 4,116,956 | 9/1978 | Meguro et al. | 260/239 |

(List continued on next page.)

FOREIGN PATENT DOCUMENTS

| | | | |
|---|---|---|---|
| 0295411 | 5/1988 | European Pat. Off. | A61K 31/445 |
| 0295411 | 12/1988 | European Pat. Off. | A61K 31/445 |
| 0368339 | 11/1989 | European Pat. Off. | A61K 31/505 |
| 0368339 | 5/1990 | European Pat. Off. | A61K 31/505 |
| 0368409 | 5/1990 | European Pat. Off. | |
| 0431942 | 12/1990 | European Pat. Off. | A61K 31/11 |
| WO9220377 | 11/1992 | WIPO | |

OTHER PUBLICATIONS

Tetrahedron Letters No. 20, pp. 1609–1612, Pergamon Press(1971). Hester, Jackson B., Duchamp, David J. Chidester, A Synthetic Approach to New 1,4–Benzodiazepine Dervatives.

J. of Med. Chem., 1977, V. 20, pp. 1694, Walser, Armin and Zenchoff, Gladys, "Quinazolines and 1,4–Benzodiazepines. 81.$^1$ s–Triazolo[4m3–a][1,4]benzodiazepines by Oxidative Cyclization of Hydrazones".

Current Ther. Res. Jun. 1976, V. 19, pp. 661–668, Nakajima; Take; Moriya; Saji; Yui; Nagawa, Pharmacological Studies on New Potent Central Depressants; 8–Chloro–6–Phenyl–4H–s–Triazolo.

(List continued on next page.)

*Primary Examiner*—D. Gabrielle Phelan
*Attorney, Agent, or Firm*—Michael J. Rafa; Paul L. Sabatine; Steven F. Stone

[57] ABSTRACT

A composition of matter for application to a body surface or membrane to administer oxybutynin by permeation through the body surface or membrane, the composition comprising, in combination the oxybutynin to be administered, in a therapeutically effective amount; and a permeation enhancing mixture comprising a monoglyceride or a mixture of monoglycerides, and a lactic ester or a mixture of lactate esters, present in specific concentrations.

17 Claims, 6 Drawing Sheets

U.S. PATENT DOCUMENTS

| | | | |
|---|---|---|---|
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,201,211 | 5/1980 | Chandrasekaran et al. | 128/268 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,440,777 | 4/1984 | Zupan | 424/274 |
| 4,464,378 | 8/1984 | Hussain | 424/260 |
| 4,468,391 | 8/1984 | Voith | 424/244 |
| 4,508,726 | 4/1985 | Coleman | 514/220 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,559,222 | 12/1985 | Enscore et al. | 424/28 |
| 4,568,343 | 2/1986 | Leeper et al. | 604/896 |
| 4,573,995 | 3/1986 | Cheng | 604/896 |
| 4,588,580 | 5/1986 | Gale et al. | 424/21 |
| 4,588,721 | 5/1986 | Mahan | 514/220 |
| 4,588,739 | 5/1986 | Glassman | 514/401 |
| 4,590,190 | 5/1986 | Saito et al. | 514/221 |
| 4,595,684 | 6/1986 | Bennett | 514/221 |
| 4,626,539 | 12/1986 | Aungst et al. | 514/282 |
| 4,634,703 | 1/1987 | Kurtz et al. | 514/252 |
| 4,645,502 | 2/1987 | Gale et al. | 604/896 |
| 4,663,454 | 5/1987 | Huber | 540/563 |
| 4,666,903 | 5/1987 | Gallager | 514/220 |
| 4,683,231 | 7/1987 | Glassman | 514/220 |
| 4,685,913 | 8/1987 | Amidon et al. | 604/892 |
| 4,704,282 | 11/1987 | Campbell et al. | 242/449 |
| 4,710,497 | 12/1987 | Heller et al. | 514/221 |
| 4,721,709 | 1/1988 | Seth et al. | 514/221 |
| 4,746,515 | 5/1988 | Cheng et al. | 424/449 |
| 4,752,612 | 6/1988 | Saito et al. | 514/420 |
| 4,783,450 | 11/1988 | Fawzi et al. | 514/78 |
| 4,783,456 | 11/1988 | Glassman | 514/214 |
| 4,788,062 | 11/1988 | Gale et al. | 424/449 |
| 4,795,644 | 1/1989 | Zentner | 424/468 |
| 4,801,458 | 1/1989 | Hidaka | 424/443 |
| 4,806,341 | 2/1989 | Chien | 424/448 |
| 4,814,183 | 3/1989 | Zentner | 424/485 |
| 4,816,258 | 3/1989 | Nedberge et al. | 424/448 |
| 4,820,720 | 4/1989 | Sanders et al. | 514/356 |
| 4,849,226 | 7/1989 | Gale | 424/448 |
| 4,851,228 | 7/1989 | Zentner et al. | 424/456 |
| 4,863,720 | 9/1989 | Burghart et al. | 424/45 |
| 4,863,738 | 9/1989 | Taskovich | 424/449 |
| 4,863,970 | 9/1989 | Patel et al. | 514/784 |
| 4,908,027 | 3/1990 | Enscore et al. | 604/890 |
| 4,908,389 | 3/1990 | Mahjour et al. | 514/772 |
| 4,913,905 | 4/1990 | Fankhauser | 424/449 |
| 4,925,844 | 5/1990 | Resch | 514/252 |
| 4,933,184 | 6/1990 | Tauk | 424/449 |
| 4,935,428 | 6/1990 | Lewis | 514/282 |
| 4,940,586 | 7/1990 | Cheng et al. | 424/464 |
| 4,943,435 | 7/1990 | Baker | 424/448 |
| 4,968,507 | 11/1990 | Zentner et al. | 424/465 |
| 4,981,468 | 1/1991 | Benefiel | 604/83 |
| 4,992,445 | 2/1991 | Lawter et al. | 514/279 |
| 4,994,278 | 2/1991 | Sablotsky et al. | 424/449 |
| 5,004,610 | 4/1991 | Osborne et al. | 424/448 |
| 5,017,575 | 5/1991 | Golwyn et al. | 514/220 |
| 5,030,629 | 7/1991 | Rajadhyaksha | 514/211 |
| 5,041,437 | 8/1991 | Yoshida et al. | 514/218 |
| 5,059,427 | 10/1991 | Yoshida et al. | 424/449 |
| 5,108,995 | 4/1992 | Casper | 514/170 |
| 5,122,382 | 6/1992 | Gale | 424/449 |
| 5,122,383 | 6/1992 | Heiber et al. | 424/449 |
| 5,149,538 | 9/1992 | Granger | 424/449 |
| 5,198,223 | 3/1993 | Gale | 424/449 |
| 5,211,952 | 5/1993 | Spicer et al. | 424/426 |
| 5,246,949 | 9/1993 | Yoshida et al. | 514/356 |
| 5,252,588 | 10/1993 | Azuma et al. | 514/317 |
| 5,256,421 | 10/1993 | Casper | 424/449 |
| 5,276,022 | 1/1994 | Casper | 514/170 |
| 5,314,694 | 5/1994 | Gale | 424/448 |
| 5,411,740 | 5/1995 | Lee et al. | 424/448 |

OTHER PUBLICATIONS

Naunyn–Schmiedeberg's Arch. Pharmacol. 301, pp. 157–161 (1978), Sethy, Vimala H. Sethy, "Effect of Hypnotic and Axiolytic Agents on Regional Concentration of Acetylcholine in Rat Brain".

Current Therapeutic Res., V. 19, No. 6, Jun. 1976, pp. 661–668, Fabre, Louis F., Jr., Pilot Open Label Study with Alprozolam (U31;889) in Outpatients with Neurotic Depression.

J. Clin. Psychiatry 42:9, Sep. 1981 pp. 347–351, Cohn, Jay B., "Multicenter Double–Blind Efficacy and Safety Study Comparing Alprazolam, Diazepam and Placebo in Clincally Anxious Patients".

J. Clin. Psychiatry, 44,45 (1983) pp. 45–47, Abernethy, Greeblatt, Divol and Shader, "Pharmacokinetics of Alprazolam".

Pharmacotherapy, 2, (1982),pp. 243–254, Fawcett and Kravitz, "Alprozolam: Pharmacokinetics, Clincial Efficacy, and Mechanism of Action".

CRC Critical Review and Therapeutic Drug Carrier Systems, vol. 4, Issue 1 (1987) pp. 13–37 Knepp, Hadgraft, Guy, "Transdermal Drug Delivery: Problems and Possibilities".

J. of Pharmaceutical Sciences, V. 64, No. 6, Jun. 1975, pp. 901–924, Idson, "Percutaneous Absorption".

J. of Pharmacology & Experimental Therapeutics, V. 256, (1990) No. 2, pp. 562–567, Noronha–Blob and Kachur, Enantiomers Oxybutynin: In Vitro Pharmacological Characterization at $M_1$, $M_2$, $M_3$ Muscarinic etc.

J. of Pharmacology & Experimental Therapeutics, V. 247, (1988) No. 3, pp. 867–872, Kachur et al., "R & S Enantiomers of Oxybutynin: Pharmacological Effects in Guinea Pig Bladder & Intestine".

1

MONOGLYCERIDE/LACTATE ESTER PERMEATION ENHANCER FOR OXYBUTYNIN

RELATED APPLICATIONS

This application is a 371 of PCT/US94/11226, filed Sep. 29, 1994, and a continuation-in-part of U.S. application Ser. No. 08/129,494, filed Sep. 29, 1993, now abandoned, which application is incorporated herein, in its entirety by reference, and benefit is claimed of its filing date.

FIELD OF THE INVENTION

This invention relates to the transdermal delivery of biologically active oxybutynin. More particularly, this invention relates to novel methods and compositions for enhancing the percutaneous absorption of oxybutynin when incorporated in transdermal drug delivery systems. More particularly, but without limitation thereto, this invention relates to the transdermal delivery of oxybutynin utilizing a permeation-enhancing mixture of a monoglyceride and a lactate ester. Still more particularly, but without limitation thereto this invention relates to the transdermal delivery of oxybutynin utilizing a permeation-enhancing mixture of a monoglyceride and a lactate ester, wherein the composition contains from 15 to 25 wt % of a monoglyceride or monoglyceride mixture and from 8 to 25 wt % of lactate ester.

BACKGROUND OF THE INVENTION

The transdermal route of parenteral delivery of drugs provides many advantages over other administrative routes, and transdermal systems for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,704,282; 4,788,062; 4,816,258; 4,849,226; 4,908,027; 4,943,435; and 5,004,610. The disclosures of the above patents are incorporated herein by reference.

In many instances, drugs which would appear to be ideal candidates for transdermal delivery are found to have such low permeability through intact skin that they cannot be delivered at therapeutically effective rates from reasonably sized systems.

In an effort to increase skin permeability, it has been proposed to pretreat the skin with various chemicals or to concurrently deliver the drug in the presence of a permeation enhancer. Various materials have been suggested for this purpose, as described in U.S. Pat. Nos. 3,472,931, 3,527,864, 3,896,238, 3,903,256, 3,952,099, 4,046,886, 4,130,643, 4,130,667, 4,299,826, 4,335,115, 4,343,798, 4,379,454, 4,405,616 and 4,746,515, all of which are incorporated herein by reference; British Pat. No. 1,001,949; and Idson, Percutaneous Absorption, J. Pharm. Sci., vol. 64, No. b6, June 1975, pp 901–924 (particularly 919–921).

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–50 cm²) is at therapeutic levels. Additionally, the enhancer, when applied to the skin surface, should be non-toxic, non-irritating on prolonged exposure and under occlusion, and non-sensitizing on repeated exposure. Preferably, it should be capable of delivering drugs without producing topical reactions, burning or tingling sensations.

The present invention greatly increases oxybutynin permeability through the skin, and also reduces the lag time between application of the oxybutynin to the skin and attainment of the desired therapeutic effect.

While it is known in the art to combine permeation enhancers, this invention utilizes a novel combination of a monoglyceride and a lactate ester. Further, the invention utilizes a specific concentration of each of the novel components. The combined effect and, further, specific concentrations of the components produce a significant and surprising improvement over use of either a monoglyceride or a lactate ester alone or the combination in nonspecified concentrations.

Neurogenic bladder disease is a disorder involving loss of control of urination. The major symptoms of this disease are urinary frequency, urinary retention or incontinence. There are two types of lesions that cause a neurogenic bladder. The first, upper motoneuron lesion, leads to hypertonia and hyperreflexia of the bladder, a spastic condition, giving rise to symptoms of urinary frequency and incontinence. The second lesion, a lower motoneuron lesion, involves hypotonia and hyporeflexia of the bladder. The major symptoms in this condition are urinary retention, since the voiding reflex has been lost, and incontinence, which occurs when the bladder "leaks", being full to overflowing.

The majority of neurogenic bladder patients have the spastic or hypertonic bladder. The clinician usually attempts to convert the condition of hyperreflexia and hypertonia to hypotonia, thereby treating the primary problem of incontinence. When the condition has been converted to hypotonia, it can be managed by intermittent catheterization. However, there is a significant population of patients who cannot be converted completely from the hypertonic to the hypotonic condition, and who still find they have to urinate every hour or are incontinent.

The use of oxybutynin chloride, as approved by the FDA in the United States, is described in the 1992 Physician's Desk Reference, pages 1332 through 1333 with reference to the drug Ditropan® manufactured by Marion Merrell Dow. Oxybutynin is normally administered to human beings orally at relatively high doses (5 mg tablets taken two to four times a day). Oxybutynin has been incorporated into tablets, capsules, granules or pills containing 1–5 mg, preferably 5 mg, of oxybutynin chloride, syrups containing 1–5 mg, preferably 5 mg, of oxybutynin chloride per 5 mL and transdermal compositions (creams or ointments) containing 1–10 weight percent ("wt %") oxybutynin chloride. See, BE 902605.

In U.S. Pat. No. 4,747,845, oxybutynin was listed as an agent that could be incorporated into a transdermal synthetic resin matrix system for extended duration drug release, but oxybutynin was not used in the device. In U.S. Pat. No. 4,928,680 oxybutynin was given as a pharmacologically active agent suitable for transdermal delivery, but as with the above reference, oxybutynin was not incorporated into the device.

Oxybutynin has been incorporated into a device having a water impermeable barrier layer, a reservoir containing oxybutynin in contact with the inner surface of the barrier layer and a removable protector layer in contact with the other surface of the reservoir. The reservoir was a polyurethane fiber mat impregnated with an aqueous solution containing 25 mg/mL of oxybutynin. The device was placed on a 20 µm thick polybutadiene film. The non-barrier carrying surface was in contact with 0.05M isotonic phosphate buffer solution. The in vitro release rate measured was approximately 12 mg over 24 hours through a 49 cm² area or 10 μg/cm²·hr. (U.S. Pat. No. 4,784,857 and EP 0 250 125).

In Pharm Res, "Development of Transdermal Delivery Systems of Oxybutynin: In-Vivo Bioavailability", P. Keshary et al, (NY)8 (10 Supp) 1991, p. S205 three types of transdermal delivery systems, using matrix-diffusion controlled and membrane-permeation controlled technologies were discussed. The in vitro permeation rate of about 9, 12 and 12 μg/cm²·hr and in vitro release rates (sink condition) of about 1160, 402 and 57.2 μg/cm²·hr were obtained from Silastic monolithic, acrylic pressure sensitive adhesive matrix and reservoir type delivery systems, respectively. In humans, steady state plasma concentrations of about 1.86 ng/mL were obtained after 6 hours of application of a single 20 cm² patch of the acrylic pressure sensitive adhesive matrix type.

While it is known in the art to formulate a dual permeation enhancer system, see eg, European patent publication numbers 0295411 and 0368339, this invention utilizes a novel combination of oxybutynin with a monoglyceride and a lactate ester. Further, the invention utilizes novel concentrations of the monoglyceride/lactate ester permeation enhancer combination. The combined effect of these two permeation enhancers and further, the specific concentrations, ie, 15 to 25 wt % of monoglyceride and 8 to 25 wt % of lactic acid ester, produces a significant and surprising improvement, ie, more than an additive effect, over use of either a monoglyceride or a lactate ester alone with oxybutynin or the combination in nonspecified concentrations.

SUMMARY OF THE INVENTION

The present invention relates to improved compositions and methods for improving the penetration of oxybutynin while producing little or no skin irritation. The system of the invention comprises a carrier or matrix adapted to be placed in oxybutynin and permeation-enhancing mixture-transmitting relation to the selected skin or other body site. The carrier or matrix contains sufficient amounts of oxybutynin and the permeation-enhancing mixture to continuously coadminister to the site, over a predetermined delivery period, oxybutynin, in a therapeutically effective amount, and the permeation-enhancing mixture of a monoglyceride and a lactate ester which are present in specific concentrations, ie, 15 to 25 wt % of monoglyceride and 8 to 25 wt % of a lactate ester, preferably 20 wt % monoglyceride and 12 wt % lactate ester, in an amount effective to enhance the permeation of the drug to the skin.

As used herein, the term "transdermal" delivery or application refers to the delivery or application of oxybutynin by passage through skin, mucosa and/or other body surfaces by topical application or by iontophoresis.

As used herein, the term "therapeutically effective" amount or rate refers to the amount or rate of oxybutynin needed to effect the desired therapeutic result.

As used herein, the term "monoglyceride" refers to glycerol monooleate, glycerol monolaurate and glycerol monolinoleate, or a mixture thereof. Monoglycerides are generally been available as a mixture of monoglycerides, with the mixture deriving its name from the monoglyceride present in the greatest amount. In a preferred embodiment of this invention, the permeation enhancer is glycerol monolaurate.

As used herein, the term "glycerol monooleate" refers to glycerol monooleate itself or a mixture of glycerides wherein glycerol monooleate is present in the greatest amount.

As used herein, the term "glycerol monolaurate" refers to glycerol monolaurate itself or a mixture of glycerides wherein glycerol monolaurate is present in the greatest amount.

As used herein, the term "glycerol monolinoleate" refers to glycerol monolinoleate itself or a mixture of glycerides wherein glycerol monolinoleate is present in the greatest amount.

As used herein, the term "lactate ester" or "lactic ester of an alcohol" refers to ethyl lactate, lauryl lactate, myristyl lactate or cetyl lactate, or a mixture thereof. Preferably, the lactate ester is lauryl lactate or ethyl lactate or a mixture thereof.

As used herein, the term "substantial portion of the time period" means at least about 60% of the time period, preferably at least about 90% of the time period. Correlatively, the term "substantially constant" means a variation of less than about ±20%, preferably less than about ±10%, over a substantial portion of the time period.

As used herein, the term "permeation enhancing mixture" refers to a mixture comprising one or more lactate esters and one or more monoglycerides. The monoglyceride or monoglyceride mixture, preferably glycerol monolaurate, is present in specific concentrations. The lactic acid ester, eg, lauryl, myristyl, cetyl, ethyl, methyl or oleic acid, benzoic acid or lactic acid is also present in specific concentrations. The monoglyceride is present in the range of about 15 to about 25 weight percent and lactate ester is present in the range of about 8 to abut 25 weight percent. More preferably, the permeation enhancer mixture by weight comprises 20% GML and 12% lauryl lactate.

As used herein, the term "predetermined delivery period" or "extended time period" refers to the delivery of oxybutynin for a time period of from several hours to seven days or longer. Preferably, the time period is from 16 hours to 3 or 4 days.

As used herein, the term "permeation enhancing amount or rate" refers to the rate or amount that provides increased permeability of the application site to oxybutynin.

As used herein, the term "poly-N-vinyl amide" means a cross-linked poly-N-vinyl amide or combination of poly-N-vinyl amide such as poly-N-vinylmethylacetamide, poly-N-vinylethylacetamide, poly-N-vinylmethylisobutyramide, poly-N-vinyl-2-pyrrolidone, poly-N-vinylpyrrolidone, poly-N-vinyl-2-piperidone, poly-N-vinyl-caprolactam, poly-N-vinyl-5-methyl-2-pyrrolidone, poly-N-vinyl-3-methyl-2-pyrrolidone, and the like. Preferably, the poly-N-vinyl amide is poly-N-vinyl-2-pyrrolidone (more preferably Polyplasdone XL®, Polyplasdone XL-10®, GAF).

The invention will be described in further detail with reference to the accompanying figures wherein:

DETAILED DESCRIPTION OF THE INVENTION

Figure 1:
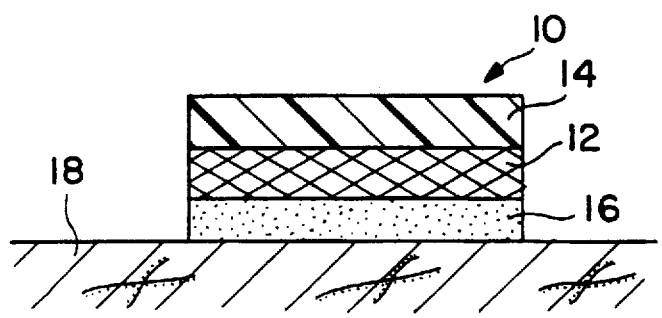
FIG. 1 is a cross-sectional view of one embodiment of the transdermal drug delivery system according to this invention.

This invention codelivers one or more monoglycerides and one or more lactate esters to aid in delivery of oxybutynin across the skin. In addition thereto, this invention calls for the monoglycerides and lactate esters to be present in specific concentrations. The combined effect and preferred concentrations according to this invention have been shown to produce dramatic increases, ie, more than an additive effect, in the permeation of oxybutynin when compared to the use of either a lactate ester or a monoglyceride alone or the two components in nonspecified concentrations. Improved enhancement of oxybutynin permeation according to this invention, can be obtained over a relatively wide concentration range of lactate ester and monoglyceride weight ratios, however, the inventors have found 20 wt % monoglyceride and 12 wt % lactate ester to provide the greatest enhancement without any negative side effects.

The present invention in one embodiment is directed to a composition of matter for application to a body surface or membrane to administer oxybutynin by permeation through the body surface or membrane, the composition comprising, in combination:

(a) the oxybutynin to be administered, in a therapeutically effective amount; and (b) a permeation-enhancing mixture comprising:
   (i) 15 to 25 wt % of a monoglyceride or a mixture of monoglycerides, and
   (ii) 8 to 25 wt % of a lactate ester or a mixture of lactate esters.

The oxybutynin may be present in the composition in an amount ranging from 0.01 to 50% by weight. The permeation-enhancing mixture preferably contains the monoglyceride and lactate ester to be present in approximately 20 wt % and 12 wt %, respectively.

This invention finds particular usefulness in enhancing permeability of oxybutynin across skin. However, it is also useful in enhancing oxybutynin flux across mucosa. Further, this invention is useful in delivery of oxybutynin both systemically and topically. According to our invention, the permeation-enhancing mixture and oxybutynin to be delivered are placed in drug- and permeation-enhancing mixture-transmitting relationship to the appropriate body surface, preferably in a pharmaceutically acceptable carrier therefor, and maintained in place for the desired period of time.

The oxybutynin and the permeation-enhancing mixture are typically dispersed within a physiologically compatible matrix or carrier as more fully described below which may be applied directly to the body as an ointment, gel, cream, suppository or sublingual or buccal tablet, for example. When used in the form of a liquid, ointment, lotion, cream or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of topical compositions as are known to the art.

In other embodiments, the oxybutynin and permeation enhancing mixture would be administered from a transdermal delivery device as more fully described below. Examples of suitable transdermal delivery devices are illustrated in FIGS. 1, 2, 3 and 4. In the drawings, the same reference numbers are used throughout the different figures to designate the same or similar components. The figures are not drawn to scale.

In FIG. 1, transdermal delivery device 10 comprises a reservoir 12 containing the oxybutynin and the permeation-enhancing mixture. Reservoir 12 is preferably in the form of a matrix containing the oxybutynin and permeation enhancing mixture dispersed therein. Reservoir 12 is sandwiched between a backing layer 14 and an in-line contact adhesive layer 16. The device 10 adheres to the surface of the skin 18 by means of the adhesive layer 16. The adhesive layer 16 may optionally contain the permeation enhancing mixture and/or oxybutynin. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16. In addition, a microporous membrane (not shown) is preferably placed on the skin-distal side of the adhesive layer.

Figure 2:
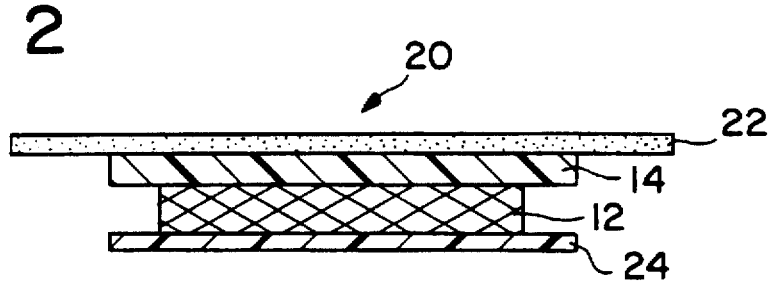
FIG. 2 is a cross-sectional view of another embodiment of the transdermal drug delivery system of this invention.

Alternatively, as shown in FIG. 2, transdermal therapeutic device 20 may be attached to the skin or mucosa of a patient by means of an adhesive overlay 22. Device 20 is comprised of a drug- and permeation enhancing mixture-containing reservoir 12 which is preferably in the form of a matrix containing the drug and the enhancing mixture dispersed therein. A backing layer 14 is provided adjacent one surface of reservoir 12. Adhesive overlay 22 maintains the device on the skin and, may be fabricated together with, or provided separately from, the remaining elements of the device. With certain formulations, the adhesive overlay 22 may be preferable to the in-line contact adhesive 16 as shown in FIG. 1. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

Figure 3:
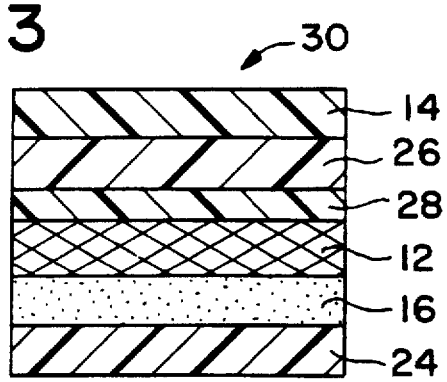
FIG. 3 is a cross-sectional view of still another embodiment of the transdermal drug delivery system according to this invention.

In FIG. 3, transdermal delivery device 30 comprises a drug- and permeation enhancing mixture-containing reservoir ("drug reservoir") 12 substantially as described with respect to FIG. 1. Permeation enhancer reservoir ("enhancer reservoir") 26 comprises the permeation enhancing mixture dispersed throughout and contains the drug at or below saturation. Enhancer reservoir 26 is preferably made from substantially the same matrix as is used to form drug reservoir 12. A rate-controlling membrane 28 for controlling the release rate of the permeation enhancer from enhancer reservoir 26 to drug reservoir 12 is placed between the two reservoirs. A rate-controlling membrane (not shown in FIG. 3) for controlling the release rate of the enhancer from drug reservoir 12 to the skin may also optionally be utilized and would be present between adhesive layer 16 and reservoir 12. In addition, a microporous membrane (not shown) may be present on the skin-distal side of adhesive layer 16.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate, ethylene n-butyl acetate and ethylene vinyl acetate copolymers.

The microporous membrane is employed as a tie layer between the drug reservoir and contact adhesive. The purpose of the layer is to reinforce the adhesion and prevent blooming and delamination of the contact adhesive from the drug reservoir layer. Blooming and delaminating are common problems when amphipathic molecules such as non-ionic surfactants, eg, monoglycerides, are utilized in the transdermal delivery devices.

A microporous tie layer should interconnect the drug reservoir and contact adhesive but should not affect the flux or release rate profiles. The layers should also have a low or negligible solubility of the surfactant or drug. The layers useful in this invention include, but are not limited to, microporous polypropylene, microporous polyethylene, microporous polycarbonate and spunbonded filamentous material.

Superimposed over the permeation enhancer reservoir 26 of device 30 is a backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12 which contains the oxybutynin and permeation enhancing mixture and bears on its surface distant from backing member 14 a rate-controlling membrane 28 for controlling the release of oxybutynin and/or permeation enhancing mixture from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

Figure 4:
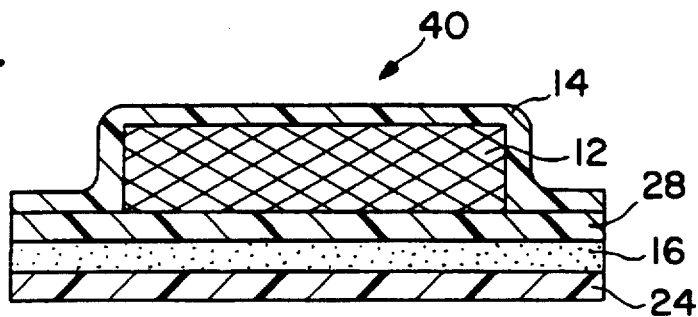
FIG. 4 is a cross-sectional view of yet another embodiment of the transdermal drug delivery system of this invention.

In an alternative embodiment of device 40 of FIG. 4, reservoir 12 contains the permeation enhancing mixture and the oxybutynin at or below saturation. Oxybutynin at or above saturation and an additional amount of permeation enhancing mixture are present in adhesive layer 16 which acts as a separate reservoir.

The oxybutynin and permeation enhancing mixture can be co-extensively administered to human skin or mucosa by direct application to the skin or mucosa in the form of an ointment, gel, cream or lotion, for example, but are preferably administered from a skin patch or other known transdermal delivery device which contains a saturated or unsaturated formulation of the drug and the enhancer. The formulation is non-aqueous based and is designed to deliver the oxybutynin and the permeation enhancing mixture at the necessary fluxes. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with both oxybutynin and the permeation enhancing mixture and any other components in the formulation.

The reservoir matrix should be compatible with oxybutynin, the permeation enhancer and any carrier therefor. The term "matrix" as used herein refers to a well-mixed composite of ingredients fixed into shape.

When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would comprise a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/oil polymers containing from 4–25% high molecular weight polyisobutylene and 20–81% low molecular weight polyisobutylene with the balance being an oil such as mineral oil or polyisobutynes may also be used as the matrix material.

The amount of oxybutynin present in the therapeutic device and required to achieve an effective therapeutic result depends on many factors, such as the minimum necessary dosage of the oxybutynin for the particular indication being treated; the solubility and permeability of the matrix, of the adhesive layer and of the rate-controlling membrane, if present; and the period of time for which the device will be fixed to the skin. The minimum amount of oxybutynin is determined by the requirement that sufficient quantities of oxybutynin must be present in the device to maintain the desired rate of release over the given period of application. The maximum amount for safety purposes is determined by the requirement that the quantity of oxybutynin present cannot exceed a rate of release that reaches toxic levels.

The oxybutynin present in the device may be either the racemate S-oxybutynin, or R-oxybutynin. Surprisingly, the inventors discovered that the flux of R- or S-oxybutynin is approximately equivalent to that of the racemate. This discovery allows for the use of a patch, when eg. only R-oxybutynin is delivered, that is at least one-half the size of the patch required to deliver the equivalent amount of the racemate.

The oxybutynin is normally present in the matrix or carrier at a concentration in excess of saturation, the amount of excess being a function of the desired length of the drug delivery period of the system. The oxybutynin may, however, be present at a level below saturation without departing from this invention as long as the drug is continuously administered to the skin or mucosal site in an amount and for a period of time sufficient to provide the desired therapeutic.

The permeation enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

The unexpected effects of the specific weight percentages of the components of the permeation enhancer mixture are believed to be due, in part, to the solubility of the monoglyceride in the lactic acid ester. It is known that monoglycerides by themselves are effective permeation enhancers. The enhancement occurs by the solubilization of the monoglyceride in the lipid layer of the skin. The solubilization of the monoglyceride in the lipid layer increases as a function of lactic acid ester concentration. For example, the solubility of glycerol monolaurate in lauryl lactate is 350 mg/g of solution when the solution is stirred. GML is practically insoluble in, for example an EVA 40 matrix. Thus, the amount of GML dissolved, ie, free GML, is dictated by and proportional to the lauryl lactate loading in the polymer.

Based on the GML solubility of 350 mg/g, free GML concentrations based upon varying weight percents of lauryl lactate in EVA 40 are as follows:

| Wt % lauryl lactate | Wt % GML in solution |
|---|---|
| 12% | 4.2% |
| 20% | 7.0% |
| 27% | 9.5% |
| 30% | 10.5% |

Thus, based upon the amount of GML in solution it would have appeared that the higher wt % of lauryl lactate would have resulted in a higher level of free GML and thus greater efficacy in increasing permeation. However, as shown by the examples, the preferred formulations, containing 20 wt % GML and 12 wt % lauryl lactate were equally effective in enhancing drug permeability as those containing 20 wt % GML and 20 wt % lauryl lactate. While the invention is directed to a permeation enhancing mixture containing a monoglyceride or monoglyceride mixture from 15 to 25 wt % and a lactic acid ester present from 8 to 25 wt %, the 20 wt % monoglyceride and 12 wt % lactic acid ester is preferred because it is as effective as the higher percentage lactic acid ester compositions, yet it delivers less of a lactic acid ester, a known potential irritant.

In addition to the oxybutynin and the permeation enhancing mixture, which are essential to the invention, the matrix or carrier may also contain dyes, pigments, inert fillers, excipients and other conventional components of pharmaceutical products or transdermal devices known to the art.

Because of the wide variation in skin permeability from individual to individual and from site to site on the same body, it may be preferable that the oxybutynin and permeation enhancing mixture be administered from a rate-controlled transdermal delivery device. Rate control can be obtained either through a rate-controlling membrane or adhesive or both as well as through the other means.

A certain amount of oxybutynin will bind reversibly to the skin, and it is accordingly preferred that the skin-contacting layer of the device include this amount of oxybutynin as a loading dose.

The surface area of the device of this invention can vary from less than 1 cm$^2$ to greater than 200 cm$^2$. A typical device, however, will have a surface area within the range of about 5–50 cm$^2$.

The devices of this invention can be designed to effectively deliver oxybutynin for an extended time period of from several hours up to 7 days or longer. Seven days is generally the maximum time limit for application of a single device because the adverse affect of occlusion of a skin site increases with time and the normal cycle of sloughing and replacement of the skin cells occurs in about 7 days.

The method of this invention comprises:
  (a) administering oxybutynin, in a therapeutically effective amount, to the area of skin over the time period; and
  (b) coadministering the permeation-enhancing mixture according to this invention to the area of skin.

Preferably, the composition delivered by this method contains a sufficient amount of permeation enhancing mixture, ie, 15 to 25 wt % of a monoglyceride or monoglyceride mixture and 8 to 25 wt % of a lactate ester and enough oxybutynin, in combination, to provide systemic administration of oxybutynin through the skin for a predetermined period of time for the oxybutynin to provide an effective therapeutic result.

The invention is also directed to a method for the transdermal administration of a therapeutically effective amount of oxybutynin together with a skin permeation-enhancing amount of a lactate ester and a monoglyceride or monoglyceride mixture preferably present in about 8 to 25 wt % and 15 to 25 wt %, respectively.

According to the present invention, it has been found that oxybutynin may be administered to the human body in a therapeutically effective amount via the transdermal route when it is coadministered with the permeation enhancing mixture. Representative skin permeation rates of oxybutynin through living human skin are in the range of about 5 µg/cm$^2$·hr to about 15 µg/cm$^2$·hr. Therapeutic blood levels can be achieved within approximately 6–10 hours after the initial application, and blood concentrations are maintained with subsequent system applications. The range of desired and achievable system permeation rates of oxybutynin, arriving through the skin from a limited area, is 1–20 mg over a period of 24 hours. The system application is easily adapted for shorter or longer duration treatments, but generally 72 hours is the duration for a single application.

A preferred embodiment of the present invention comprises a method of treating neurogenic bladder disorders, eg, urinary frequency or incontinence. To be useful in treating a neurogenic bladder disorder, oxybutynin should be present in plasma at levels above about 0.5 ng/mL, preferably at levels above about 1 ng/mL and most preferably at levels of about 2–4 ng/mL. To achieve this result, oxybutynin is delivered at a therapeutic rate of at least about 40–200 µg per hour, but typically of at least 80 µg/hr, and more typically at about 80–160 µg/hr, for the treatment period, usually about 24 hours to 7 days.

The length of time of oxybutynin presence and the total amount of oxybutynin in the plasma can be changed following the teachings of this invention to provide different treatment regimens. Thus, they can be controlled by the amount of time during which exogenous oxybutynin is delivered transdermally to an individual or animal.

Preferably, a device for the transdermal administration of oxybutynin, at a therapeutically effective rate, comprises:
  (a) a reservoir comprising:
    (i) 5 to 40% by weight oxybutynin, (ii) 15 to 25% by weight monoglyceride or mixture of monoglycerides, (iii) 8 to 25% by weight lactic acid ester, and (iv) 10 to 72% by weight ethylene vinyl acetate copolymer;

(b) a backing on the skin-distal surface of the reservoir; and (c) means for maintaining the reservoir in drug- and permeation enhancing mixture-transmitting relation with the skin.

In one embodiment, the device further comprises a microporous membrane on the skin-distal surface of the means for maintaining the reservoir in place. Preferably, the monoglyceride is glycerol monolaurate and the lactic acid ester is lauryl lactate. In another preferred embodiment, the oxybutynin is R-oxybutynin.

More preferably, a device for the transdermal administration of oxybutynin, at a therapeutically effective rate, comprises:

(a) a reservoir comprising:
(i) 15 to 30% by weight oxybutynin,
(ii) 15 to 25% by weight glycerol monolaurate,
(iii) 8 to 25% by weight lauryl lactate, and
(iv) 20 to 62% by weight ethylene vinyl acetate copolymer;

(b) a backing on the skin-distal surface of the reservoir; and (c) means for maintaining the reservoir in drug- and permeation enhancing mixture-transmitting relation with the skin.

Preferably, the device further comprises a microporous membrane on the skin-distal surface of the means for maintaining the reservoir in place. In another preferred embodiment, the oxybutynin is R-oxybutynin.

Still more preferably, a device for the transdermal administration of oxybutynin, at a therapeutically effective rate, comprises:

(a) a reservoir comprising:
(i) 20 to 25% by weight oxybutynin,
(ii) 20% by weight glycerol monolaurate,
(iii) 12% by weight lauryl lactate, and
(iv) 43 to 48% by weight ethylene vinyl acetate copolymer;

(b) a backing on the skin-distal surface of the reservoir; and (c) means for maintaining the reservoir in drug- and permeation enhancing mixture-transmitting relation with the skin.

Preferably, the device further comprises a microporous membrane on the skin-distal surface of the means for maintaining the reservoir in place. In another preferred embodiment, the oxybutynin is R-oxybutynin.

In another embodiment, the reservoir further comprises 5–25% most preferably, about 20% by weight cross-linked poly-N-vinyl-2-pyrrolidone, eg, N-vinyl-2-pyrrolidone Polyplasdone XL-10®, GAF). Preferably, the backing is a breathable backing, such as NRU-100-C® (Flexcon, Spencer, Mass.). If an occluded backing is used, preferably it is Medpar® (3M, St. Paul, Minn.). Preferably, the means for maintaining the reservoir in drug and permeation enhancing mixture transmitting relation with the skin is an acrylic contact adhesive, such as MSP041991P, 3M. Preferably, the ethylene vinyl acetate copolymer has a acetate content of 33% or 40%.

The aforementioned patents describe a wide variety of materials which can be used for fabricating the various layers or components of the transdermal drug delivery devices according to this invention. This invention therefore contemplates the use of materials other than those specifically disclosed herein, including those which may hereafter become known to the art to be capable of performing the necessary functions. The following examples are offered to illustrate the practice of the present invention and are not intended to limit the invention in any manner.

EXAMPLE 1

The drug/permeation enhancer reservoir was prepared by mixing ethylene vinyl acetate copolymer having a vinyl acetate content of 40 percent ("EVA 40", U.S.I. Chemicals, Illinois) in an internal mixer (Bra Bender type mixer) until the EVA 40 pellets fused. Oxybutynin, glycerol monolaurate and lauryl lactate were then added. The mixture was blended, cooled and calendered to a 6 mil thick film. The compositions of the reservoirs are given in Table 1.

TABLE 1

Drug/Permeation Enhancer Reservoir Composition (weight percent)

Figure 5:
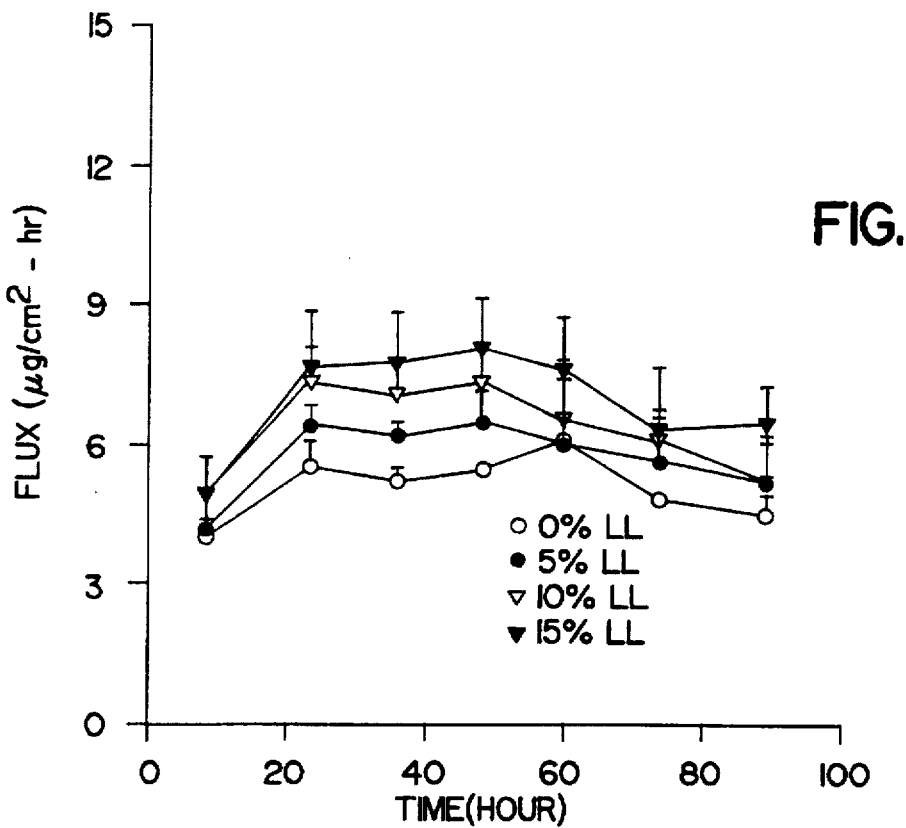
FIG. 5 is a graph of the flux of oxybutynin through human epidermis at 35° C., in vitro, with glycerol monolaurate and lauryl lactate.

| FIG. 5 |
| --- |
| oxybutynin/glycerol monolaurate/EVA 40 (25/15/60) |
| oxybutynin/glycerol monolaurate/lauryl lactate/EVA 40 (25/15/5/55) |
| oxybutynin/glycerol monolaurate/lauryl lactate/EVA 40 (25/15/10/50) |
| oxybutynin/glycerol monolaurate/lauryl lactate/EVA 40 (25/15/15/45) |

Figure 6:
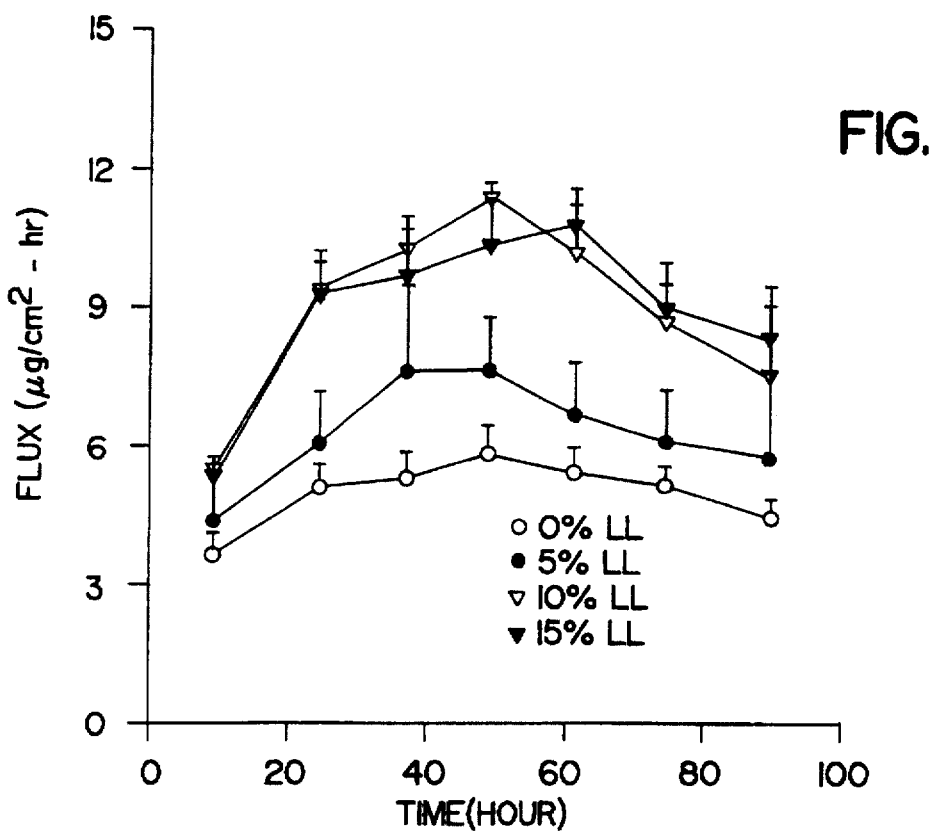
FIG. 6 is a graph of the flux of oxybutynin through human epidermis at 35° C., in vitro, with glycerol monolaurate and lauryl lactate.

| FIG. 6 |
| --- |
| oxybutynin/glycerol monolaurate/EVA 40 (25/20/55) |
| oxybutynin/glycerol monolaurate/lauryl lactate/EVA 40 (25/20/5/50) |
| oxybutynin/glycerol monolaurate/lauryl lactate/EVA 40 (25/20/10/45) |
| oxybutynin/glycerol monolaurate/lauryl lactate/EVA 40 (25/20/15/40) |

Figure 7:
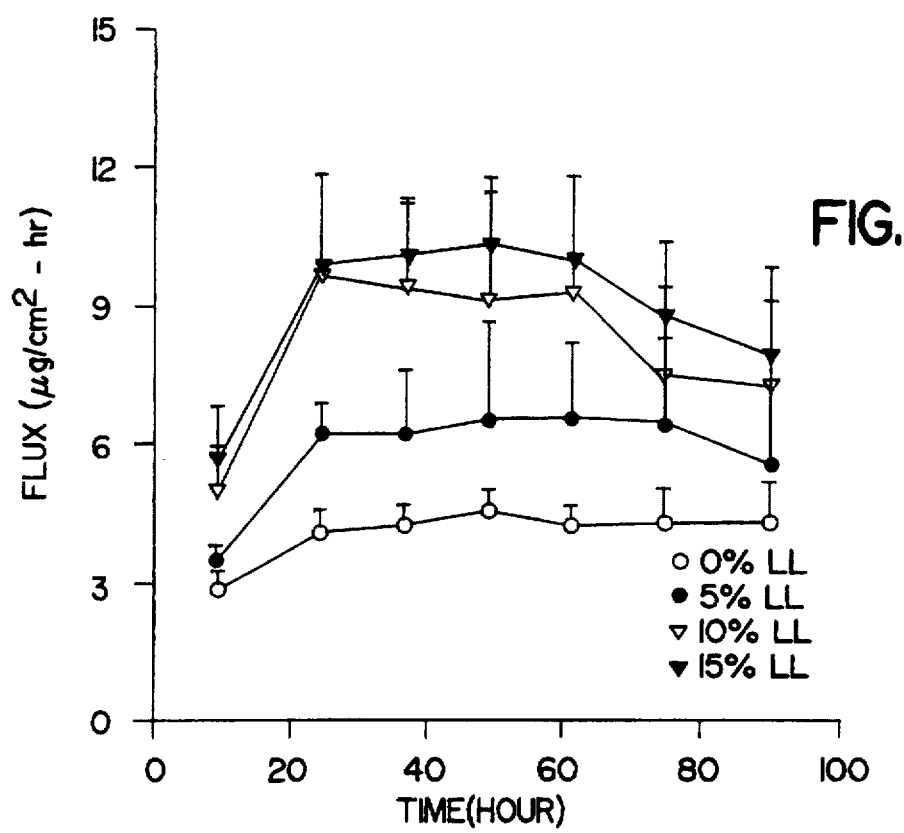
FIG. 7 is a graph of the flux of oxybutynin through human epidermis at 35° C., in vitro, with glycerol monolaurate and lauryl lactate.

| FIG. 7 |
| --- |
| oxybutynin/glycerol monolaurate/EVA 40 (25/25/50) |
| oxybutynin/glycerol monolaurate/lauryl lactate/EVA 40 (25/25/5/45) |
| oxybutynin/glycerol monolaurate/lauryl lactate/EVA 40 (25/25/10/40) |
| oxybutynin/glycerol monolaurate/lauryl lactate/EVA 40 (25/25/15/35) |

This film was then laminated to an acrylic contact adhesive (MSP041991P, 3M) on one side and Medpar® backing (3M) on the opposite side. The laminate was then cut into 2.54 cm² circles using a stainless steel punch.

Circular pieces of human-epidermis were mounted on horizontal permeation cells with the stratum corneum facing the donor compartment of the cell. The release liner of the system was then removed and the system was centered over the stratum corneum side of the epidermis. A known volume of the receptor solution (0.05M sodium phosphate buffer at pH 6) that had been equilibrated at 35° C. was placed in the receptor compartment. Air bubbles were removed; the cell was capped and placed in a water bath-shaker at 35° C.

At given time intervals, the entire receptor solution was removed from the cells and replaced with an equal volume of fresh receptor solutions previously equilibrated at 35° C.

The receptor solutions were stored in capped vials at 4° C. until assayed for oxybutynin content by HPLC.

From the drug concentration and the volume of the receptor solutions, the area of permeation and the time interval, the flux of the drug through the epidermis was calculated as follows: (drug concentration×volume of receptor/(area×time)=flux ($\mu g/cm^2 \cdot hr$).

The fluxes achieved for the different systems are shown in FIGS. 5, 6 and 7. The fluxes for the devices that contained glycerol monolaurate and lauryl lactate were higher on average than the fluxes obtained from the devices that contained only glycerol monolaurate.

Figure 8:
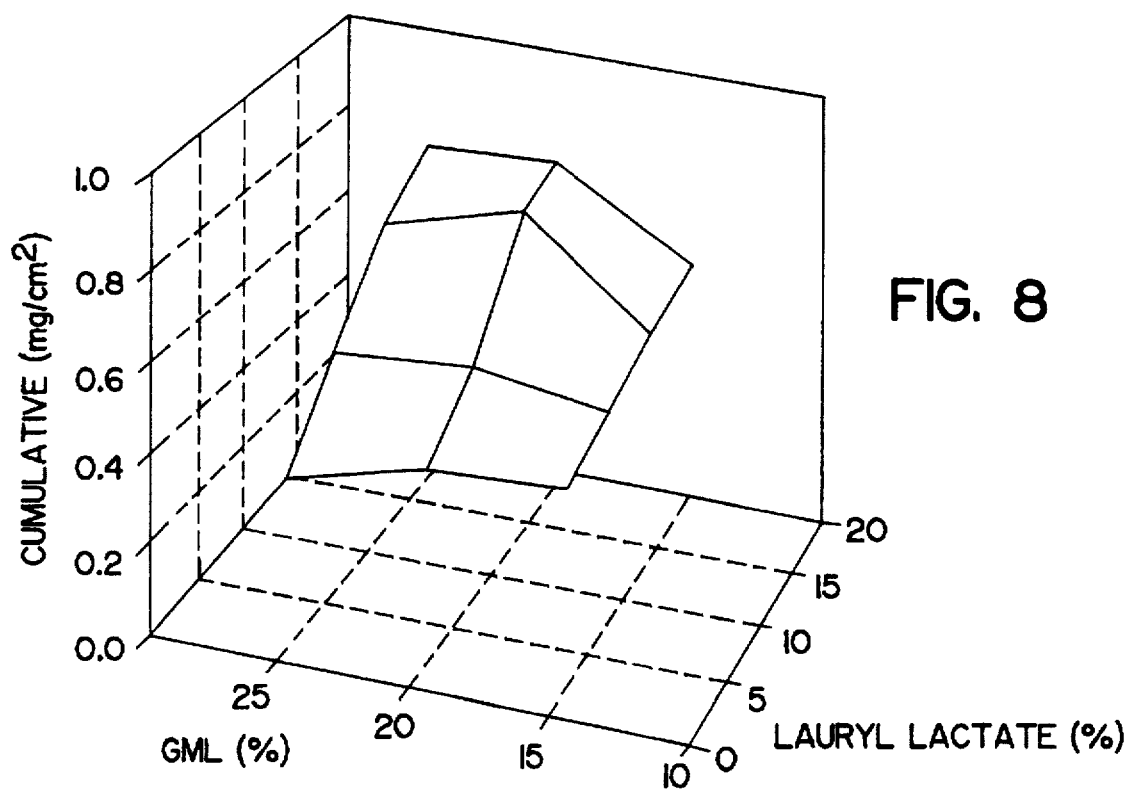
FIG. 8 is a graph of the cumulative amount of oxygen through human epidermis with varying glycerol monolaurate and lauryl lactate.
Figure 9:
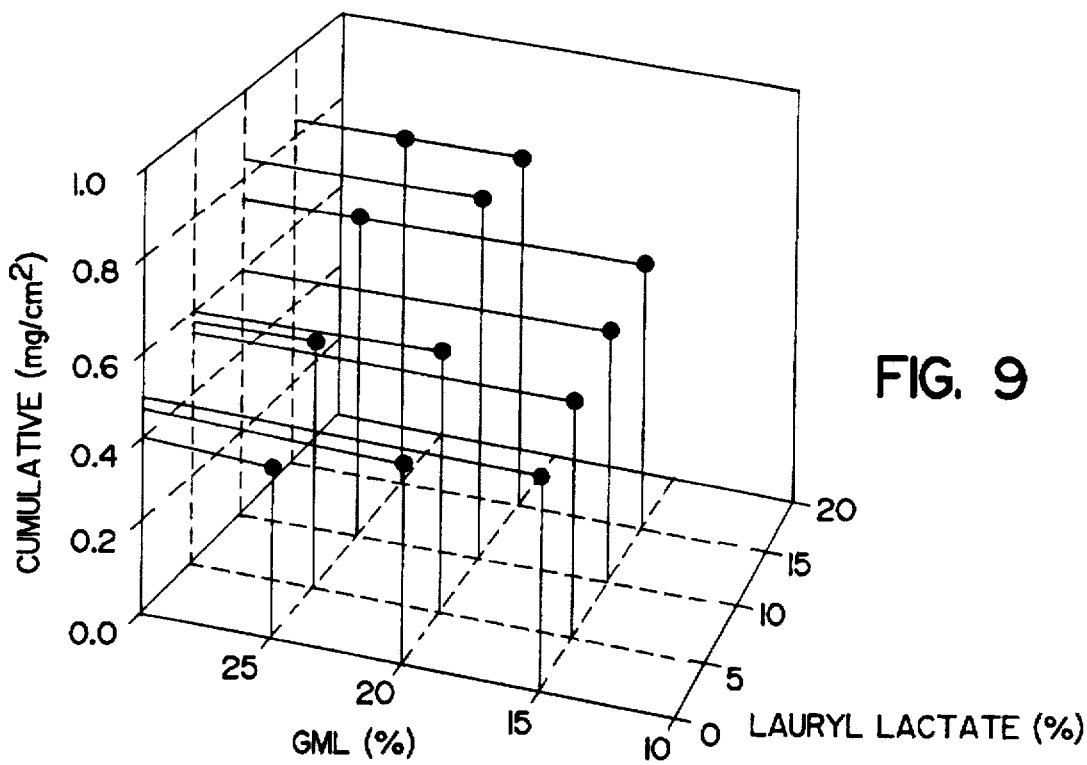
FIG. 9 is a graph of the cumulative amount of oxygen through human epidermis with varying glycerol monolaurate and lauryl lactate.

FIGS. 8 and 9 are 3-dimensional depictions of the data displayed in FIGS. 5-7, ie, the varying amounts of GML, lauryl lactate and the cumulative flux of oxybutynin. As depicted by the Figs., 20% by weight GML and 12% by weight lauryl lactate provides the greatest flux enhancement.

EXAMPLE 2

The drug/permeation enhancer reservoir was prepared by mixing ethylene vinyl acetate copolymer having a vinyl acetate content of 40 percent ("EVA 40", U.S.I. Chemicals, Illinois) in an internal mixer (Bra Bender type mixer) until the EVA 40 pellets fused. Oxybutynin, glycerol monolaurate and lauryl lactate were then added. The mixture was blended, and calendered to a 5.0 mil thick film. The compositions of the reservoir is given in Table 2.

TABLE 2

| Drug/Permeation Enhancer Reservoir Composition (weight percent) | | | |
|---|---|---|---|
| Oxybutynin | Glycerol Monolaurate | Lauryl Lactate | EVA-40 |
| 25 | 15 | 0 | 60 |
| 25 | 15 | 5 | 55 |
| 25 | 15 | 10 | 50 |
| 25 | 15 | 15 | 45 |
| 25 | 20 | 0 | 55 |
| 25 | 20 | 5 | 50 |
| 25 | 20 | 10 | 45 |
| 25 | 20 | 15 | 40 |

This film was then laminated to an acrylic contact adhesive (MSP041991P, 3M) on one side and a Medpar® or NRU-100-C® backing (Flexco Co.) on the opposite side. The film was then cut into circles and taped to prevent release of drug from the system edge.

For each device tested, the adhesive was placed against the stratum corneum side of a disc of human epidermis that had been blotted dry just prior to use. The excess epidermis was wrapped around the device so that none of the device edge was exposed to the receptor solution. The device covered with epidermis was attached to the flat side of the Teflon holder of a release rod using nylon netting and nickel wire. The rods were reciprocated in a fixed volume of receptor solution (0.05M sodium phosphate buffer at pH 6). The entire receptor solution was changed at each sampling time. The temperature of the receptor solution in the water bath was maintained at 35° C.

Figure 10:
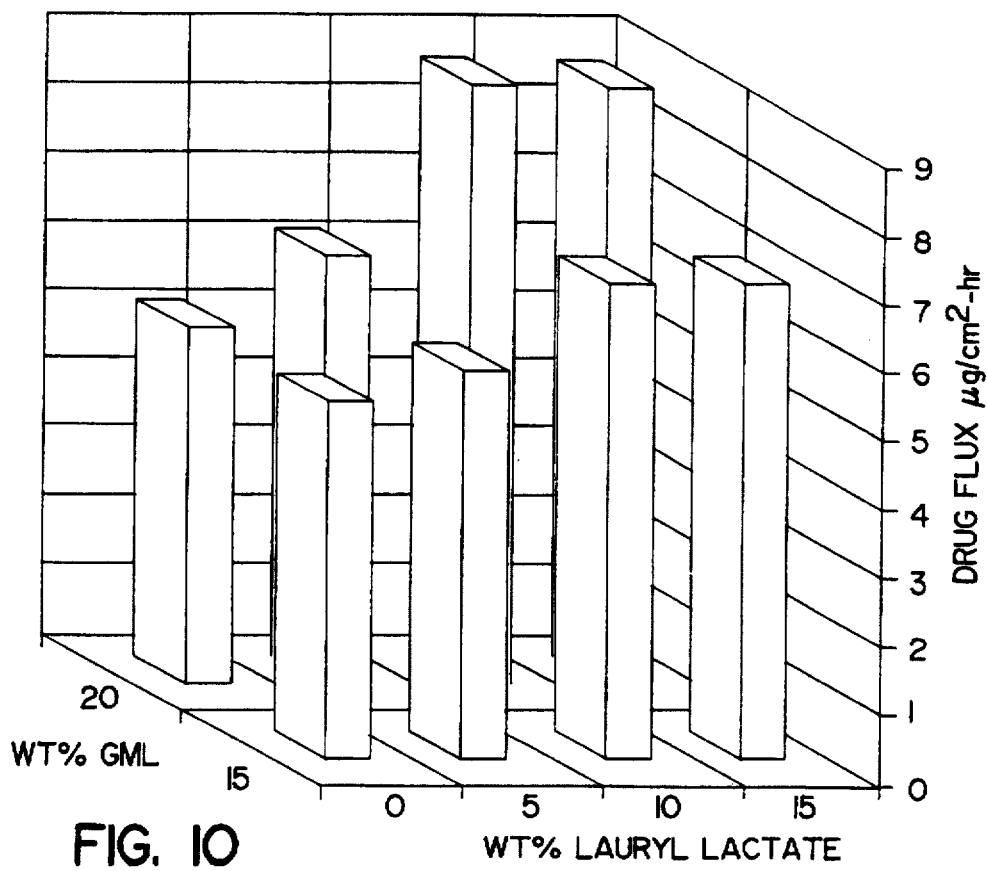
FIG. 10 is a bar graph of the effect of glycerol monolaurate and lauryl lactate on the flux of oxybutynin through human epidermis at 35° C., in vitro.

The receptor solutions were stored in capped vials at 4° C. until assayed for oxybutynin content by HPLC. The fluxes achieved for the different systems were calculated and are shown in FIG. 10.

EXAMPLE 3

The drug/permeation enhancer reservoir was prepared by mixing ethylene vinyl acetate copolymer having a vinyl acetate content of 40 percent ("EVA 40", U.S.I. Chemicals, Illinois) in an internal mixer (Bra Bender type mixer) until the EVA 40 pellets fused. Oxybutynin, glycerol monolaurate and lauryl lactate were then added. The mixture was blended, and calendered to a 5 mil thick film. The compositions of the reservoir are given in Table 3.

TABLE 3

| Drug/Permeation Enhancer Reservoir Composition (weight percent) | | | |
|---|---|---|---|
| Oxybutynin | Glycerol Monolaurate | Lauryl Lactate | EVA-40 |
| 25 | 20 | 12 | 43 |

This film was then laminated to an acrylic contact adhesive (MSP04199P, 3M) on one side and spun-lace polyester backing, Sontara NRU-100-C® backing (Flexco Co.) on the opposite side. One-half of the samples also included a microporous polypropylene membrane (Celgard®, Hoechst Celanese) laminated to the skin-distal side of the contact adhesive. The film was then cut into circles and taped to prevent edge release.

For each device tested, the adhesive was placed against the stratum corneum side of a disc of human epidermis that had been blotted dry just prior to use. The excess epidermis was wrapped around the device so that none of the device edge was exposed to the receptor solution. The device covered with epidermis was attached to the flat side of the Teflon holder of a release rod using nylon netting and nickel wire. The rods were reciprocated in a fixed volume of receptor solution (0.05M sodium phosphate buffer at pH 6). The entire receptor solution was changed at each sampling time. The temperature of the receptor solution in the water bath was maintained at 35° C.

Figure 11:
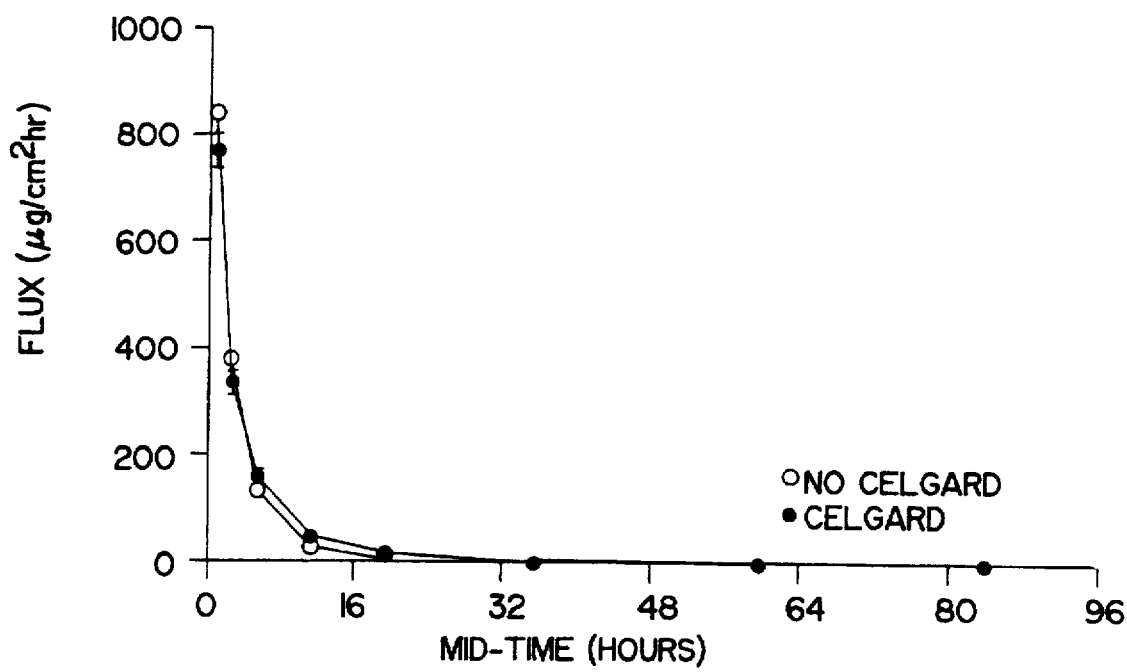
FIG. 11 is a graph of the effect of a microporous membrane on the rate of oxybutynin.
Figure 12:
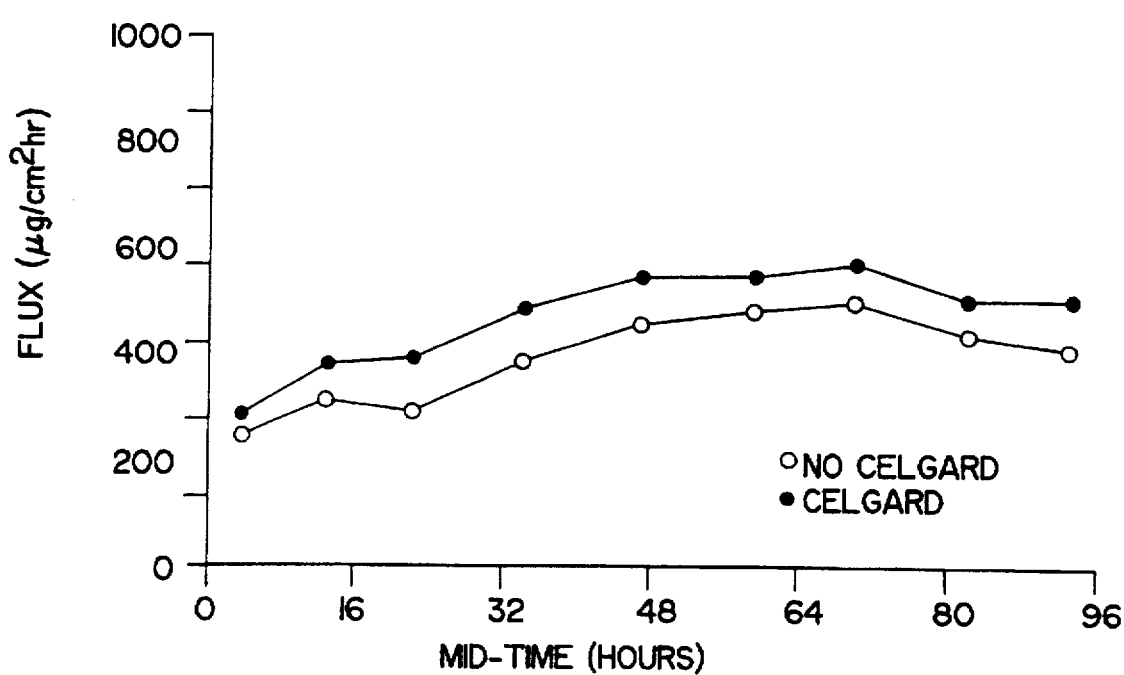
FIG. 12 is a graph of the effect of a microporous membrane on the flux of oxybutynin through human epidermis at 35° C., in vitro.
Figure 13:
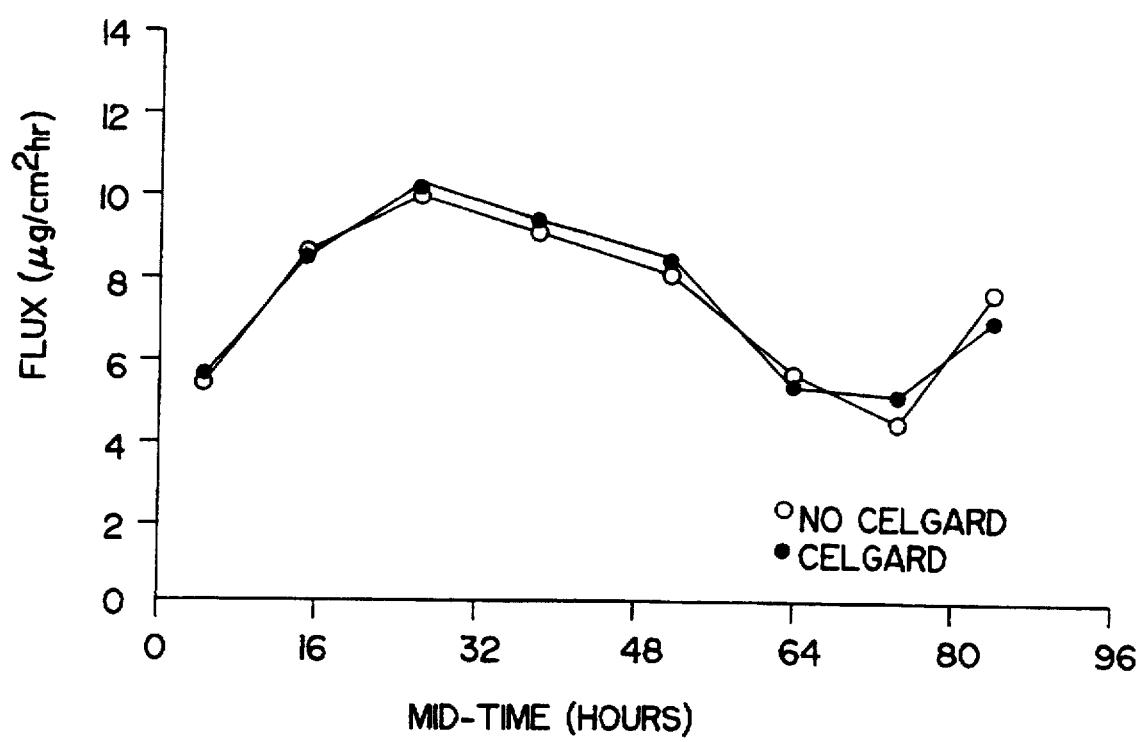
FIG. 13 is a graph of the effect of a microporous membrane on the flux of oxybutynin through human epidermis at 35° C., in vitro.

The receptor solutions were stored in capped vials at 4° C. until assayed for oxybutynin content by HPLC. The effect of the Celgard® on the fluxes and release rates achieved for the different systems is shown in FIGS. 11–13.

EXAMPLES 4–5

The drug/permeation enhancer reservoir was prepared by mixing, depending on the formulation, either ethylene vinyl acetate copolymer having a vinyl acetate content of 40 percent ("EVA 40", U.S.I. Chemicals, Illinois) or mineral oil and petrolatum in an internal mixer (Bra Bender type mixer) until the EVA 40 pellets fused. Oxybutynin, glycerol monolaurate and lauryl lactate were then added.

When EVA 40 was used the mixture was blended, cooled and calendered to a 5 mil thick film. This film was then laminated to an acrylic contact adhesive (MSP041991P, 3M) on one side and Medpar® backing (3M) on the opposite side. The laminate was then cut into 2.54 cm² circles using a stainless steel punch. Circular pieces of human-epidermis were mounted on horizontal permeation cells with the stratum corneum facing the donor compartment of the cell. The release liner of the system was then removed and the system was centered over the stratum corneum side of the epidermis. A known volume of the receptor solution (0.05M sodium phosphate buffer at pH 6) that had been equilibrated at 35° C. was placed in the receptor compartment. Air bubbles were removed; the cell was capped and placed in a water bath-shaker at 35° C.

When the mineral oil/petrolatum was used, the mixture, containing the drug and permeation enhancers, was blended/ mixed and then poured into the donor side of a two-side diffusion cell. Pieces of human epidermis were mounted between the two sides of the diffusion cell. A known volume of the receptor solution (0.05M sodium phosphate buffer at pH 6) that had been equilibrated at 35° C. was placed in the receptor compartment. Air bubbles were removed; the cell was capped and placed in a water bath-shaker at 35° C.

At given time intervals, the entire receptor solution for either system was removed from the cells and replaced with an equal volume of fresh receptor solutions previously equilibrated at 35° C. The receptor solutions were stored in capped vials at 4° C. until assayed for oxybutynin content by HPLC.

The permeation rates achieved for the different systems are shown in Table 4, along with the drug reservoir composition. The fluxes for the devices/gels that contained only one enantiomer were approximately equivalent to those obtained from devices/gels containing the racemate mixture.

TABLE 4

| Drug/Permeation Enhancer Reservoir Composition | Oxybutynin Permeation Rate at Study State (µg/h · cm$^2$) |
| --- | --- |
| Mineral Oil/Petrolatum/GML/LL/R-oxybutynin 32/11/20/12/25 | 12 |
| Mineral Oil/Petrolatum/GML/LL/S-oxybutynin 32/11/20/12/25 | 13 |
| Mineral Oil/Petrolatum/GML/LL/oxybutynin (racemate) 21/11/20/12/25 | 11 |
| EVA-40/GML/LL/oxybutynin (racemate) 43/20/12/25 | 6 |
| EVA-40/GML/LL/R-oxybutynin 43/20/12/25 | 4 |
| EVA-40/GML/LL/S-oxybutynin 43/20/12/25 | 4 |

This invention has been described in detail with particular reference to certain preferred embodiments thereof, but it will be understood that variations and modifications can be effected within the spirit and scope of the invention.

What is claimed is:

1. A composition of matter for application to a body surface or membrane to administer oxybutynin by permeation through the body surface or membrane, the composition comprising, in combination:
   (a) oxybutynin to be administered, in a therapeutically effective amount; and
   (b) a permeation-enhancing mixture comprising:
      (i) 20 wt % of a monoglyceride or a mixture of monoglycerides, and
      (ii) 12 wt % of a lactate ester or a mixture of lactate esters.

2. A composition according to claim 1 wherein the lactate ester is selected from the group consisting of lauryl lactate, ethyl lactate, myristyl lactate, or cetyl lactate.

3. A composition according to claim 1 wherein the mixture of lactate esters is ethyl lactate and lauryl lactate.

4. A composition according to claims 2 or 3 wherein the monoglyceride is glycerol monolaurate.

5. A device for the transdermal administration of oxybutynin at a therapeutically effective rate, which device comprises:

(a) an oxybutynin reservoir comprising a therapeutically effective amount of oxybutynin and a skin permeation-enhancing amount of a permeation mixture comprising:
   (i) 20 wt % of a monoglyceride or a mixture of monoglycerides, and
   (ii) 12 wt % of a lactate ester or a mixture of lactate esters;
(b) a backing on the skin-distal surface of the reservoir; and
(c) means for maintaining the oxybutynin reservoir in drug and permeation enhancing mixture-transmitting relation with the skin.

6. A device according to claim 5 further comprising a second reservoir positioned between the backing and the oxybutynin reservoir, the second reservoir comprising an excess of the permeation enhancing mixture and oxybutynin at or below saturation; and a rate-controlling membrane between the oxybutynin reservoir and the second reservoir.

7. A device according to claims 5 or 6 further comprising a microporous membrane on the skin-distal side of the maintaining means.

8. A device according to claims 5 or 6 wherein the monoglyceride or mixture of monoglycerides comprises 20 wt % and the lactate ester comprises 12 wt %.

9. A device according to claims 5 or 6 wherein the monoglyceride is glycerol monolaurate.

10. A device according to claims 5 or 6 wherein the lactate ester is selected from the group consisting of lauryl lactate, ethyl lactate, cetyl lactate or myristyl lactate.

11. A device according to claims 5 or 6 wherein the mixture of lactate esters is ethyl lactate and lauryl lactate.

12. A device according to claims 5 or 6 wherein the monoglyceride is glycerol monolaurate and the lactate ester is ethyl lactate or lauryl lactate or a mixture thereof.

13. A device according to claims 5 or 6 wherein the drug is R-oxybutynin.

14. A device according to claim 6 wherein the oxybutynin reservoir also is an adhesive layer which functions as the means for maintaining the reservoirs in relation with the skin.

15. A device according to claim 10 wherein the monoglyceride is glycerol monolaurate.

16. A device according to claim 5 or 6 wherein the oxybutynin reservoir comprising 20–62% by weight ethylene vinyl acetate copolymer.

17. A method for the transdermal administration of oxybutynin which method comprises:
   (a) administering oxybutynin at a therapeutically effective rate to an area of skin; and
   (b) simultaneously administering a permeation enhancing mixture comprising:
      (i) 20 wt % of a monoglyceride or a mixture of monoglycerides, and
      (ii) 12 wt % of a lactate ester or a mixture of lactate esters;
   to the area of skin at a rate which is sufficient to substantially increase the permeability of the area to the drug.

* * * * *